United States Patent
Ayala et al.

(10) Patent No.: US 11,406,473 B2
(45) Date of Patent: Aug. 9, 2022

(54) ENGRAVED RETRO-REFLECTIVE TRACKING MARKER

(71) Applicant: Brainlab AG, Munich (DE)

(72) Inventors: Andrew Ayala, Munich (DE); Jimena Saldivar, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 16/499,417

(22) PCT Filed: Aug. 29, 2018

(86) PCT No.: PCT/EP2018/073225
§ 371 (c)(1),
(2) Date: Sep. 30, 2019

(87) PCT Pub. No.: WO2020/043278
PCT Pub. Date: Mar. 5, 2020

(65) Prior Publication Data
US 2021/0401535 A1    Dec. 30, 2021

(51) Int. Cl.
*A61B 90/00* (2016.01)
*A61B 34/20* (2016.01)
*B29D 11/00* (2006.01)

(52) U.S. Cl.
CPC .............. *A61B 90/39* (2016.02); *A61B 34/20* (2016.02); *B29D 11/00605* (2013.01);
(Continued)

(58) Field of Classification Search
CPC . A61B 5/0261; A61B 5/0037; A61B 5/02444; A61B 5/7425; A61B 34/20;
(Continued)

(56) References Cited

U.S. PATENT DOCUMENTS

| 6,725,083 | B1 * | 4/2004 | Burbank ................ A61B 90/39 600/431 |
| 7,688,998 | B2 | 3/2010 | Tuma et al. |

(Continued)

FOREIGN PATENT DOCUMENTS

| EP | 0203752 A2 | 12/1986 |
| EP | 1563799 A1 | 8/2005 |

(Continued)

OTHER PUBLICATIONS

European Office Action for corresponding European application No. 18765398.5, dated Dec. 19, 2019. 6 pages.
(Continued)

*Primary Examiner* — Joel Lamprecht
(74) *Attorney, Agent, or Firm* — Tucker Ellis LLP

(57) ABSTRACT

The present invention relates to a method of producing an optically detectable and retro-reflective medical tracking marker, wherein electromagnetic energy is applied to at least one section of a retro-reflective surface of a marker structure in an amount that is sufficient to alter the material properties of the retro-reflective surface, such that the capability of reflecting electromagnetic radiation of the at least one section is reduced to a second capability of reflecting electromagnetic radiation. The present invention further relates to a corresponding retro-reflective medical tracking marker and a corresponding use thereof.

20 Claims, 4 Drawing Sheets

(52) U.S. Cl.
CPC . *A61B 2034/2055* (2016.02); *A61B 2090/397* (2016.02); *A61B 2090/3937* (2016.02)

(58) Field of Classification Search
CPC ....... A61B 90/361; A61B 90/37; A61B 90/39; A61B 2034/2055; A61B 2090/371; A61B 2090/373; A61B 2090/3983; A61B 5/746; A61B 2505/05; A61B 5/14542; A61B 5/0295; A61B 5/1032; A61B 5/743; A61B 5/02416; A61B 5/0275; G06T 7/0012; G06T 2207/30004; G06T 2207/30048; G06T 2207/30061; G06T 2207/30101; G06T 2207/30104; G16H 30/00; G16H 40/60; G16H 40/63
See application file for complete search history.

(56) References Cited

U.S. PATENT DOCUMENTS

2013/0190616 A1* 7/2013 Casanova .............. A61B 90/39
600/431
2014/0340750 A1 11/2014 Neal et al.
2015/0196369 A1* 7/2015 Glossop ................ A61B 5/064
600/409

FOREIGN PATENT DOCUMENTS

WO   95/25970 A1   9/1995
WO   2010027646 A1   3/2010

OTHER PUBLICATIONS

International Search Report and Written Opinion for corresponding international application No. PCT/EP2018/073225, dated May 28, 2019. 12 Pages.

* cited by examiner

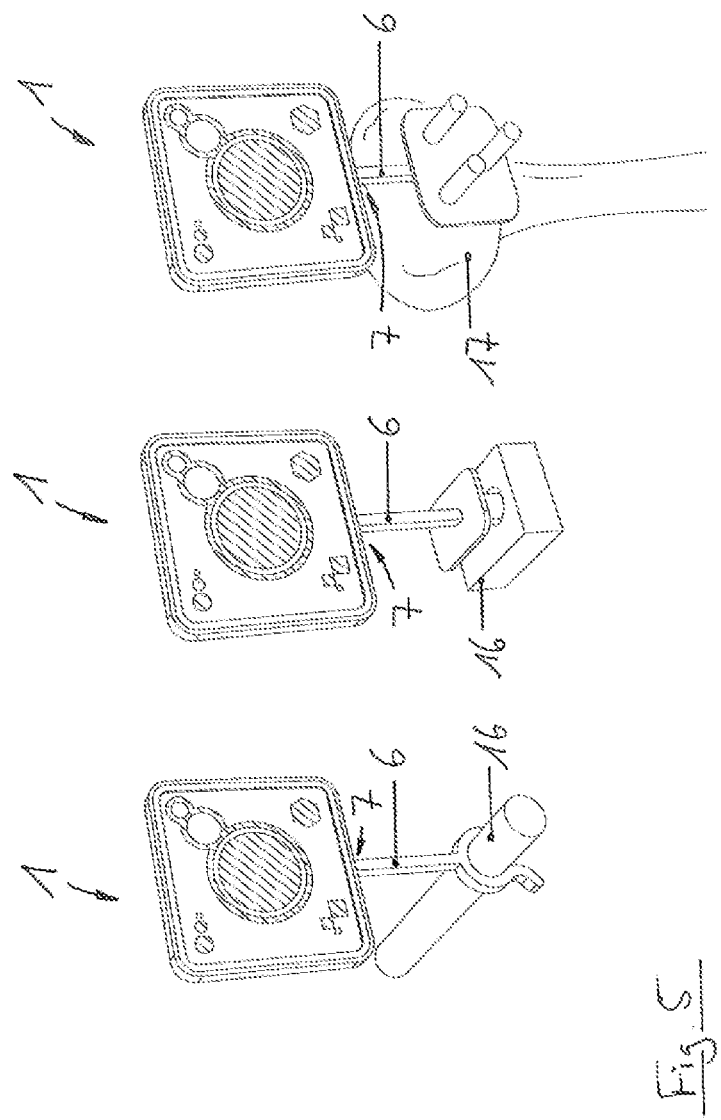

ENGRAVED RETRO-REFLECTIVE TRACKING MARKER

RELATED APPLICATION DATA

This application is a national phase application of International Application No. PCT/EP2018/073225 filed Aug. 29, 2018, the contents of which are incorporated herein by reference.

FIELD OF THE INVENTION

The present invention relates to a method for producing an optically detectable tracking marker for medical purposes, and further to such optically detectable tracking marker and the use thereof during a medical procedure.

TECHNICAL BACKGROUND

The use of tracking markers is widely known in the field of medical procedures such as computer assisted surgery (CAS), which require that the position of objects, for example anatomical structures and medical instruments can be precisely determined in a three-dimensional space where the medical procedure takes place.

It is the purpose of a medical tracking marker that the spatial position (including the spatial location and/or the spatial orientation) of objects is determinable by a computer system. In order to fulfil this purpose, such tracking markers are usually rigidly attached to the respective objects and are further adapted to be detected by a corresponding tracking system. While there are different types of tracking markers known in the art, which make use of different physical principles, the present invention relates to the type of optically detectable tracking markers, i.e. tracking markers which are detectable by tracking systems that comprise light susceptible cameras. More specifically, the present invention relates to passive tracking markers, i.e. which are adapted to reflect electromagnetic radiation in the infrared, visible and/or ultraviolet spectral range. In order to increase the reflective properties, such markers can be provided with a retro-reflective surface which is adapted to reflect incoming light back in substantially the opposite direction it came from. Such retro-reflective properties are for example known from so-called "cat's eyes" or high-visibility vests.

Commonly used retro-reflective tracking marker have a spherical shape and are therefore often called marker spheres. As optical cameras will detect such marker spheres from any direction as a circular disk, such that the spatial location of the central point of this disk is basically the only exploitable information for the tracking system, determining the spatial position of objects with up to 6 degrees of freedom requires an array of at least three marker spheres to be rigidly attached to the object the spatial position has to be determined of.

The present invention has the object of providing an optically detectable and retro-reflective medical tracking marker which is capable of providing additional information to a medical tracking system. To this end, the present invention can be used for any optical tracking system, particularly for medical tracking systems distributed by Brainlab AG.

Aspects of the present invention, examples and exemplary steps and their embodiments are disclosed in the following. Different exemplary features of the invention can be combined in accordance with the invention wherever technically expedient and feasible.

GENERAL DESCRIPTION OF THE INVENTION

In general, the invention reaches the aforementioned object by providing, in a first aspect, a method of producing an optically detectable and retro-reflective medical tracking marker, wherein the method comprises the following steps:

providing a marker structure comprising a retro-reflective surface that has a first capability of reflecting electromagnetic radiation;

applying electromagnetic energy to at least one section of the retro-reflective surface in an amount that is sufficient to alter the material properties of the retro-reflective surface, such that the capability of reflecting electromagnetic radiation of the at least one section is reduced to a second capability of reflecting electromagnetic radiation.

In other words, the surface of the tracking marker, which has the above explained retro-reflective properties, is treated in predefined areas with electromagnetic radiation to such an extent, that the former retro-reflective properties are reduced in the predefined areas, such that the surface of the tracking marker finally comprises at least one predefined area the retro-reflective properties of which are reduced as compared to the remaining, untreated surface of the tracking marker. With the surface of the tracking marker having now at least two predefined sections with different retro-reflective capabilities, it is now possible that the marker surface carries additional information for an optical tracking system. For example, the treated section with a reduced capability of reflecting light may have a certain shape, size or position on the marker surface, which can be recognized by the tracking system and which may encode and/or store further information that can be processed by a medical navigation system.

For example, the capability of reflecting electromagnetic radiation of the treated section is substantially eliminated by applying said electromagnetic energy. Thus, the treated sections or areas of the marker surface may appear substantially black on the images provided by a camera of the tracking system.

Further, said electromagnetic energy may be applied via a laser-beam. In this context, it is important to note that the invention allows for an extraordinary preciseness, not only in producing a tracking marker, but also by providing a tracking marker with sharply delineated surface sections which in turn facilitate the optical tracking as a whole.

In a further example, the location, orientation, size and/or shape of the at least one section of the retro-reflective surface is predefined with respect to the geometry of the marker structure. In other words, the one or more treated sections of the marker surface may be calibrated with respect to the marker structure, which allows that a series of markers can be produced, all of which have predictably arranged sections of a reduced or even eliminated capability of reflecting light.

In a further example, the at least one treated section is arranged in a predefined manner with respect to a mechanical interface of the marker structure, which is adapted to attach the marker either directly or indirectly via a support structure to an object to be spatially tracked. In that case, the tracking marker can be pre-calibrated, such that the spatial position of objects of a predefined geometry, particularly medical instruments, which are fitted with such a marker can be immediately determined without having to perform a calibration procedure.

Further, the method of producing the tracking marker may further comprise the step of applying a transparent layer or coating to the marker structure, which covers the retro-reflective surface. Such transparent layer may be formed by a flexible film or a rigid pane and serves, just like a transparent coating, as a protective cover for the retro-reflective surface. Further, the electromagnetic energy applied to the retro-reflective surface to reduce or substantially eliminate the retro-reflective capabilities in at least one predefined section can be applied through the transparent layer or coating that already covers the retro-reflective surface.

For example, at least two separate retro-reflective sections of the marker surface remain untreated after the electromagnetic energy has been applied, which then of course have the initial capability of reflecting light.

In such case, it is possible to provide different information to different retro-reflective sections. For example, the location, orientation, size and/or shape of at least one first retro-reflective section is adapted to codify the specific identity of the tracking marker. In other words, the at least one first section contains information as to the specific type or properties of the tracking marker or may even codify the unique identity of the very tracking marker it is attached to. On the other hand, the location, orientation, size and/or shape of at least one second retro-reflective section is adapted to define the spatial location and/or orientation of the tracking marker. Of course, just the other way around, it is also possible to provide distinct information via distinct treated sections with reduced or eliminated retro-reflective properties, for example by codifying this information via the location, orientation, size and/or shape of those sections.

Moreover, the method-step of providing the marker structure together with the retro-reflective surface may involve the steps of:

providing a two-dimensional retro-reflective film; and
applying the retro-reflective film to the marker structure.

In other words, the marker structure may serve as a substrate for a retro-reflective film that is glued or otherwise attached to the surface of the marker structure, particularly to a flat surface of the marker structure.

The retro-reflective film may however also be glued or otherwise applied to a non-flat surface of the marker structure, particularly to a spherical surface of the marker structure from which a marker sphere may then be obtained.

For the benefit of a highly accurate, precise and repeatable production of the inventive tracking marker, the retro-reflective film may be applied to the marker structure before the electromagnetic energy, particularly laser light is applied to the retro-reflective film.

The retro-reflective marker surface, particularly the retro-reflective film applied to the marker structure may comprise a plurality of elements of a transparent material, which have a substantially spherical shape and which are retained by a matrix. The effect, the invention makes use of by applying electromagnetic energy to the retro-reflective surface or film may then be at least one of the following:

the spherical shape of the elements being altered or destroyed;
the fixation of the elements by the matrix being destroyed;
the color and/or material properties of the matrix being altered.

While in the first case microscopic glass or plastic spheres can be burst, deformed or melted, the second case may include that such spheres drop out of the supporting matrix. Considering the effect on the matrix, the applied electromagnetic energy or laser light may blacken or burn the matrix material such that, particularly in addition to the lost or destroyed transparent spheres, the capability of the retro-reflective surface or film in reflecting light is also reduced.

Coming back to accuracy, preciseness and repeatability of in particular producing the inventive tracking marker, the marker structure can be positioned with respect to a device for applying the electromagnetic energy, with at least one reference surface of the marker structure contacting at least one corresponding reference surface assigned to the device. In other words, the marker structure may have at least one reference surface with which it is brought into contact with corresponding surface(s) having a predefined spatial position with respect to the beam source. Consequently, the beam of electromagnetic energy or light can be positioned in an accurate, precise and repeatable manner with respect to the marker structure, such that the treated and untreated areas of the retro-reflective surface are eventually located in a definite manner with respect to the marker structure.

In a second aspect, the invention relates to a medical tracking marker having an optically detectable and retro-reflective surface, wherein the retro-reflective surface has a first capability of reflecting electromagnetic radiation, and at least one section having a second capability of reflecting electromagnetic radiation, wherein the material properties of the retro-reflective surface have been altered in the at least one section by applying electromagnetic energy, such that the capability of reflecting electromagnetic radiation of the at least one section is reduced to the second capability of reflecting electromagnetic radiation.

In particular, this marker can be obtained or produced by a method in accordance with the first aspect of the invention as explained further above.

In a third aspect, the invention relates to the use of a tracking marker according to the second aspect for high precision tracking during a medical procedure involving an optical tracking system, particularly for position and/or motion tracking of a surgical instrument;
position and/or motion tracking of an anatomical structure of a patient;

and/or for determining topological information during a medical procedure involving an optical tracking system.

For example, the invention does not involve or in particular comprise or encompass an invasive step which would represent a substantial physical interference with the body requiring professional medical expertise to be carried out and entailing a substantial health-risk even when carried out with the required professional care and expertise.

In this respect, the present invention improves the use of tracking markers not only for medical procedures but also for any technical appliance for which objects have to be tracked in a three-dimensional space, since the present invention fulfills the highest requirements of intrinsic and extrinsic accuracy, color-contrast and contour quality.

BRIEF DESCRIPTION OF THE DRAWINGS

In the following, the invention is described with reference to the appended figures which give background explanations and represent specific embodiment of the invention.

The scope of the invention is however not limited to the specific features disclosed in the context of the figures, wherein

FIG. 5 shows different appliances for the medical tracking marker according to the present invention.

DESCRIPTION OF EMBODIMENTS

Figure 1:
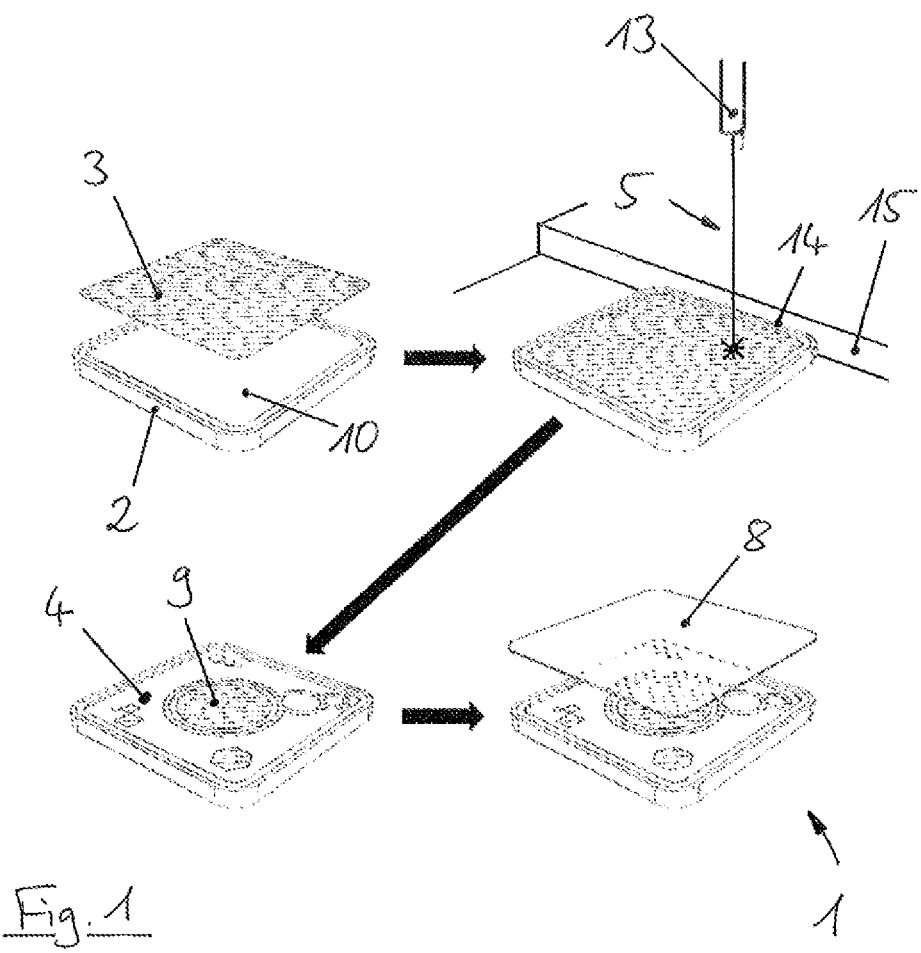
FIG. 1 illustrates the basic steps of the inventive method of producing a medical tracking marker.

FIG. 1 illustrates the basic steps of the method according to a first aspect. Starting with the top left illustration, a retro-reflective film 3 is glued onto a flat surface 10 of a rigid marker structure 2 which from now on serves as a substrate for the retro-reflective film.

In a later step (top right in FIG. 1), the marker structure 2 is positioned with respect to a laser beam source 13 by bringing one of its outer reference surfaces 14 that frame the marker structure 2 into contact with a corresponding reference surface 15 that in turn takes a predefined position with respect to the laser beam source 13. Thus, the pattern engraved into the retro-reflective surface 3 by the laser beam 5 is calibrated with respect to the reference surface 14 of the marker structure 2.

In the specific example shown in FIG. 1, the laser-engraved pattern comprises sections 4 with a substantially eliminated capability of reflecting light, along with untreated sections 9 with an unamended capability of reflecting light (see bottom left illustration in FIG. 1).

In a later, final step, a protective transparent film 8 is glued, welded or otherwise attached to the substrate 2, such that it covers the retro-reflective film 3.

Figure 2:
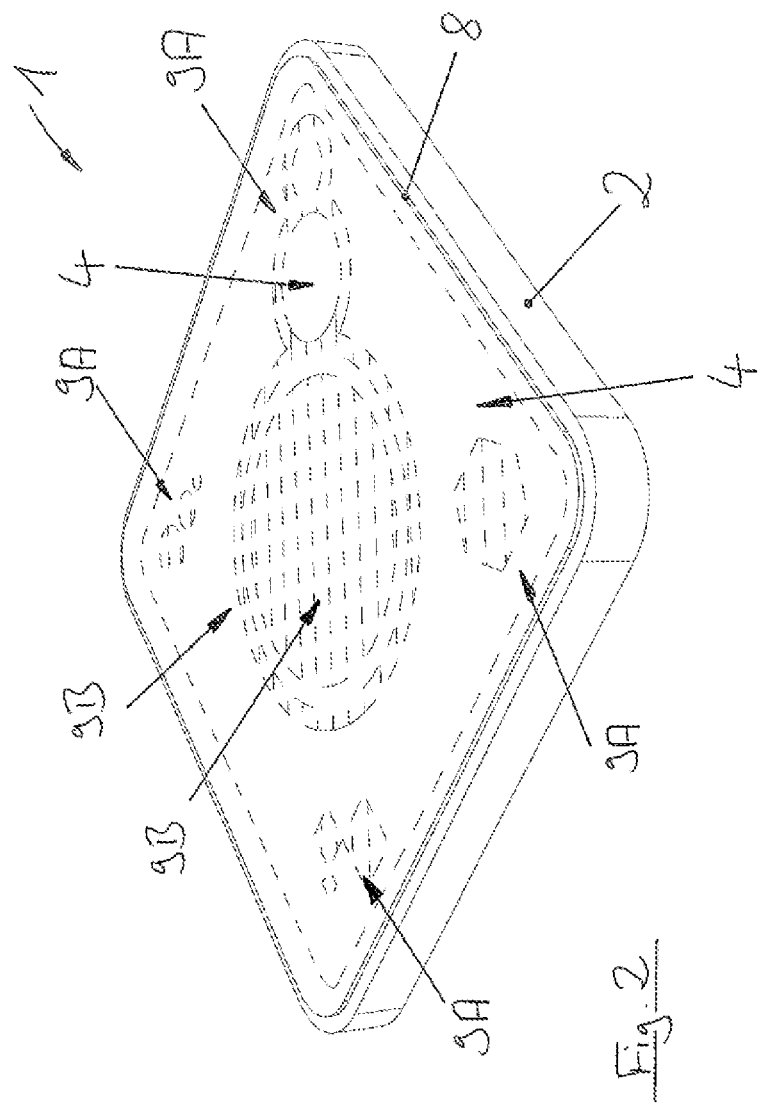
FIG. 2 shows a tracking marker according to the present invention obtained by the method illustrated in FIG. 1.

FIG. 2 shows a specific example of the inventive tracking marker 1, comprising a marker structure 2 with a specific pattern engraved into a retro-reflective film 3 underneath a transparent layer 8.

A plurality of sections 9A is provided in the edges of the substantially square-shaped film 3, such that a medical tracking system can determine from the location, orientation, size and/or shape of these sections 9A appearing in the camera image, how the tracking marker 1 is located and oriented in three-dimensional space.

On the other hand, the retro-reflective surface 3 comprises two concentric sections 9B which codify the specific identity of the tracking marker shown in FIG. 2.

In a further embodiment, instead of or in additional to such circles, sections are provided inside of circles or other forms that codify the specific identity of the tracking marker.

Figure 3:
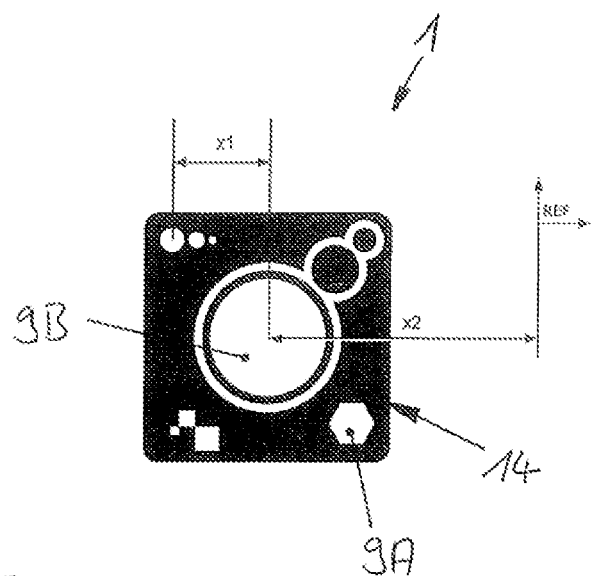
FIG. 3 shows an example of a retro-reflective pattern of the medical tracking marker according to the present invention.

FIG. 3 again shows the specific marker pattern of FIG. 2 and further illustrates that the sections 9A and 9B are positioned at predefined distances (X1, X2) with respect to a spatial reference (REF). In particular, anyone of the reference surfaces 14 of the marker structure 2 can represent a spatial reference REF for positioning the sections 9A and 9B.

Figure 4:
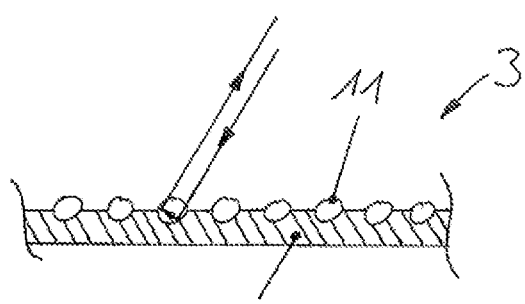
FIG. 4 shows a cross-section of a retro-reflective surface or layer.

FIG. 4 illustrates the operating principle of retro-reflective surfaces. In contrast to a mere mirror, which reflects an incoming light-ray at an angle which is mirror-symmetrical to the angle direction of the incoming light-ray, a retro-reflective surface is adapted to reflect incoming light in substantially the opposite direction it came from. In the shown example, an incoming light-ray entering a glass-sphere 11 retained in a matrix 12 is reflected twice at the boundary interface of the glass-sphere 11, before it exits the glass sphere 11 in the opposite direction it initially came from. Of course, the glass spheres 11 may be substituted by any other element which is capable of retro-reflecting light, for example structures with orthogonal boundary interfaces such as glass cubes or pyramids.

FIG. 5 shows different appliances for the inventive medical tracking marker. In the illustration on the left, the support structure 6 of the tracking marker 1 is merely clamped onto a rod-shaped and rotationally symmetrical medical instrument, such that the tracking marker 1 which is fixed to the support structure 6 via the interface 7 can freely rotate around the longitudinal axis of the instrument 16. In this case, one single tracking marker 1 is sufficient to determine 5 degrees of freedom of the instrument's 16 spatial position in three-dimensional space.

The same applies to the appliances shown in the center and the right illustration, except for the fact that the marker 1 in the center illustration is freely rotatable around the longitudinal axis of the support structure 6, and that the tracking marker 1 in the right illustration is fixedly attached to the anatomical structure 17, such that it allows for determining 6 degrees of freedom of the anatomical structure 17 in three-dimensional space.

The invention claimed is:

1. A method of producing an optically detectable and retro-reflective medical tracking marker, comprising:
   providing a marker structure comprising a retro-reflective surface that comprises a plurality of elements of a transparent material, each of the plurality of elements having a spherical shape and being retained by a matrix, the retro-reflective surface configured to reflect incoming electromagnetic radiation with a first intensity; and
   applying electromagnetic energy to at least one section of the retro-reflective surface thereby altering material properties of the retro-reflective surface of the at least one section such that the at least one section is configured to reflect incoming electromagnetic radiation with a second intensity, the second intensity being lower than the first intensity.

2. The method according to claim 1, wherein the at least one section of the retro-reflective surface has a reduced capability of reflecting electromagnetic radiation as compared to sections of the retro-reflective surface not treated with application of electromagnetic energy, wherein the reduced capability includes a substantially eliminated capability of reflecting electromagnetic radiation.

3. The method according to claim 1, wherein the electromagnetic energy is applied via a laser-beam.

4. The method according to claim 1, wherein a location, orientation, size and/or shape of the at least one section of the retro-reflective surface is predefined with respect to a geometry of the marker structure.

5. The method according to claim 1, further comprising applying a transparent layer or coating to the marker structure, which covers the retro-reflective surface.

6. The method according to claim 1, wherein:
   the applying the electromagnetic energy to at least one section of the retro-reflective surface leaves at least one first retro-reflective section and at least one second retro-reflective section, the at least one first retro-reflective section and the at least one second retro-reflective section having the first capability of reflecting electromagnetic radiation,
   a location, orientation, size and/or shape of the at least one first retro-reflective section codifies a specific identity of the tracking marker, and
   a location, orientation, size and/or shape of the at least one second retro-reflective section enables a medical tracking system to detect a spatial location and/or orientation of the tracking marker.

7. The method according to claim 1, wherein the providing the marker structure comprising the retro-reflective surface involves:
   providing a two-dimensional retro-reflective film; and
   applying the two-dimensional retro-reflective film to the marker structure.

8. The method according to claim 7, wherein the two-dimensional retro-reflective film is glued to a flat surface of the marker structure.

9. The method according to claim 7, wherein the two-dimensional retro-reflective film is stretched over and glued to a three-dimensional spherical surface of the marker structure.

10. The method according to claim 7, wherein the two-dimensional retro-reflective film is applied to the marker structure before the electromagnetic energy is applied to at least one section of the retro-reflective surface.

11. The method according to claim 7, wherein the second capability of reflecting electromagnetic radiation results from at least one of:
   the spherical shape of at least one of the plurality of elements being altered or destroyed responsive to the application of electromagnetic energy;
   the retention of at least one of the plurality of elements by the matrix being destroyed responsive to the application of electromagnetic energy;
   a color and/or a material property of the matrix being altered responsive to the application of electromagnetic energy.

12. The method according to claim 1, further comprising positioning the marker structure with respect to a device for applying the electromagnetic energy, with at least one reference surface of the marker structure contacting at least one corresponding reference surface assigned to the device.

13. The method according to claim 4, wherein the retro-reflective surface is predefined with respect to a mechanical interface of the marker structure, which is adapted to attach the optically detectable and retro-reflective medical tracking marker to a support structure.

14. The method according to claim 5, wherein the electromagnetic energy is applied to the retro-reflective surface through the transparent layer or the coating.

15. The method according to claim 12, wherein the device is a laser.

16. A medical tracking marker comprising:
   a marker structure; and
   a retro-reflective surface, the retro-reflective surface comprising:
      a matrix;
      a plurality of elements of a transparent material, each of the plurality of elements having a spherical shape and being retained by the matrix;
      a first section, wherein the first section of the retro-reflective surface is configured to reflect incoming electromagnetic radiation with a first intensity; and
      a second section, wherein the second section of the retro-reflective surface is configured to reflect incoming electromagnetic radiation with a second intensity, the second intensity being lower than the first intensity as a result of an electromagnetic energy treatment to the second section altering material properties of the matrix and/or the plurality of elements of the transparent material within the second section.

17. The medical tracking marker according to claim 16, wherein the retro-reflective surface comprises a two-dimensional retro-reflective film.

18. The medical tracking marker according to claim 17, wherein the two-dimensional retro-reflective film is stretched over a surface of the marker structure.

19. The medical tracking marker according to claim 16, wherein the altered material properties of the matrix and/or the plurality of elements of the transparent material within the second section comprises at least one of:
   an altered or destroyed spherical shape of at least one of the plurality of elements;
   a destroyed retention of at least one of the plurality of elements by the matrix;
   an altered color and/or a material property of the matrix.

20. A system comprising:
   a laser; and
   a medical tracking marker comprising:
      a marker structure; and
      a retro-reflective surface, the retro-reflective surface comprising:
         a matrix;
         a plurality of elements of a transparent material, each of the plurality of elements having a spherical shape and being retained by the matrix;
         a first section, wherein the first section of the retro-reflective surface is configured to reflect incoming electromagnetic radiation with a first intensity; and
         a second section, wherein the second section of the retro-reflective surface is configured to reflect incoming electromagnetic radiation with a second intensity, the second intensity being lower than the first intensity as a result of an electromagnetic energy treatment by the laser, to the second section, altering material properties of the matrix and/or the plurality of elements of the transparent material within the second section.

* * * * *